(12) United States Patent
Lambris et al.

(10) Patent No.: US 9,579,360 B2
(45) Date of Patent: Feb. 28, 2017

(54) METHODS OF TREATING OR PREVENTING PERIODONTITIS AND DISEASES ASSOCIATED WITH PERIODONTITIS

(71) Applicant: The Trustees of the University of Pennsylvania, Philadelphia, PA (US)

(72) Inventors: John D. Lambris, Philadelphia, PA (US); George Hajishengallis, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/801,096

(22) Filed: Mar. 13, 2013

(65) Prior Publication Data

US 2013/0344082 A1   Dec. 26, 2013

Related U.S. Application Data

(60) Provisional application No. 61/662,022, filed on Jun. 20, 2012.

(51) Int. Cl.
*A61K 38/12* (2006.01)
*G01N 33/50* (2006.01)
*A61K 39/395* (2006.01)

(52) U.S. Cl.
CPC .......... *A61K 38/12* (2013.01); *A61K 39/3955* (2013.01); *G01N 33/502* (2013.01); *G01N 2333/4716* (2013.01); *G01N 2800/18* (2013.01)

(58) Field of Classification Search
None
See application file for complete search history.

(56) References Cited

U.S. PATENT DOCUMENTS

| 5,270,365 | A | 12/1993 | Gertz et al. | |
| 2010/0166862 | A1* | 7/2010 | Francois et al. | 424/484 |
| 2014/0371133 | A1* | 12/2014 | Francois | A61K 38/12 514/1.7 |

FOREIGN PATENT DOCUMENTS

| WO | WO 2010056399 A1 * | 5/2010 |
| WO | WO 2010/132954 A1 | 11/2010 |
| WO | WO 2011/091366 A2 | 7/2011 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Ma (Modern Drug Discovery 2004, 7(6)).*
Ricklin et al (Adv Exp Med Biol. 2008; 632: 273-292).*
Qu et al (Immunobiology. Apr. 2013;218(4):496-505. Epub Jun. 17, 2012).*
Oz et al (J Biomed Biotechnol. 2011;2011:754857. Epub Feb. 10, 2011).*
Aagaard et al (Advanced Drug Delivery Reviews 59 (2007) 75-86).*
Warzocha et al (Leukemia and Lymphoma, Val. 24. pp. 267-281).*
American Dental Association (ADA), Treating Periodontal Diseases, JADA, vol. 136, Jan. 2005.*
Warzocha et al (Leukemia and Lymphoma, (1997) vol. 24. pp. 267-281).*
Armitage, G., "Classifying periodontal diseases—a long-standing dilemma," *Periodontology 2000*, (2002), vol. 30, pp. 9-23.
Awano, S., et al., "Oral health and mortality risk from pneumonia in the elderly," *J Dent, Res.*, (2008), vol. 87, pp. 334-339.
Beikler, T., et al., "Gene expression in periodontal tissues following treatment," *BMC Medical Genomics*, (2008), vol. 1, 1-9.
Beikler, T., et al., "Oral biofilm-associated diseases: trends and implications for quality of life, systemic health and expenditures," *Periodontology 2000*, (2011), vol. 55, pp. 87-103.
Bostanci, N., et al.,"*Porphyromonas gingivalis*: an invasive and evasive opportunistic oral pathogen," *FEMS Microbiol. Lett.*, (May 2012), vol. 333, pp. 1-9.
Brown, L.J., et al., "The economics of periodontal diseases," *Periodontology 2000*, (2002), vol. 29, pp. 223-234.
Davey, M.E., et al., "Molecular genetics analyses of biofilm formation in oral isolates," *Periodontology 2000*, (2006), vol. 42, pp. 13-26.
Demmer, R.T., et al., "Epidemiologic patterns of chronic and aggressive periodontitis," *Periodontology 2000*, (2010), vol. 53, pp. 28-44.
Gaffen, S.L., et al., "A new inflammatory cytokine on the block: Re-thinking periodontal disease and the Th1/Th2 paradigm in the context of Th17 cells and IL-17," *J. Dent. Res.*, (2008), vol. 87, pp. 817-828.
Genco, R.J., et al., "Reducing the risk of CVD in patients with periodontitis," *Nat. Rev. Cardiol.*, (2010), vol. 7, pp. 479-480.
Graves, D.T., et al., "The use of rodent models to investigate host-bacteria interactions related to periodontal diseases," *J. Clin. Periodontal.*, (2008), vol. 35, pp. 89-105.
Hajishengallis, G., "Complement and periodontitis," *Biochem. Pharmacol.*, (2010), vol. 80, pp. 1992-2001.
Hajishengallis, G., et al., "Crosstalk pathways between Toll-like receptors and the complement system," *Trends Immunol.*, (2010), vol. 31, pp. 154-163.
Hajishengallis, G., et al., "Low-abundance biofilm species orchestrates inflammatory periodontal disease through the commensal microbiota and complement," *Cell Host & Microbe*, (2011), vol. 10, pp. 497-506.
Jeffcoat, M., et al., "Periodontal infection and preterm birth; successful periodontal therapy reduces the risk of preterm birth," *BJOG*, (2011), vol. 118, pp. 250-256, Published online Sep. 15, 2010.
Kim, D.H., et al., "RNAi mechanisms and applications," *Biotechniques*. (2008); vol. 44, pp. 613-616.
Krayer, J.W., et al., "Non-surgical chemotherapeutic treatment strategies for the management of periodontal diseases," *Dent. Clin. North Am.*, (2010), vol. 54, pp. 13-33.
Lalla, E., et al., "Diabetes mellitus and periodontitis: a tale of two common interrelated diseases," *Nat. Rev. Endocrinology*, (2011), vol. 7, pp. 738-748.

(Continued)

*Primary Examiner* — Brian J Gangle
*Assistant Examiner* — Andrea McCollum

(57) ABSTRACT

The present disclosure describes methods for preventing or treating periodontitis or diseases associated with periodontitis. The present disclosure also describes methods of screening for compounds that can be used to prevent or treat periodontitis or diseases associated with periodontitis.

6 Claims, 9 Drawing Sheets

(56) References Cited

OTHER PUBLICATIONS

Lares, M.R., et al., RNAi and small interfering RNAs in human disease therapeutic applications, *Trends Biotechnol.*, (2010), vol. 28, pp. 570-579.

Lundberg, K., et al., "Periodontitis in RA—the citrullinated enolase connection," *Nat. Rev. Rheumatology*, (2010), vol. 6, pp. 727-730.

Nikolopoulou-Papaconstantinou, A.-A., et al., "Deposits of immunoglobulins, complement, and immune complexes in inflamed human gingiva," *Acta Odontol. Scand.*, (1987), vol. 45, pp. 187-193.

Patters, M.R., et al., "Assessment of complement cleavage in gingival fluid during experimental gingivitis in man," *J. Clin. Periodontol.*, (1989), vol. 16, pp. 33-37.

Pfeifer, A., et al., "Pharmacological potential of RNAi—focus on miRNA", *Pharmacology & Therapeutics*, (2010), vol. 126, pp. 217-227.

Pihlstrom, B.L., et al., "Periodontal diseases," *Lancet*, (2005), vol. 366, pp. 1809-1820.

Qu, H., et al., "New analogs of the clinical complement inhibitor compstatin with subnanomolar affinity and enhanced pharmacokinetic properties," *Immunobiology*, (2013), vol. 218, pp. 496-505.

Ricklin, D., et al., "Complement: a key system for immune surveillance and homeostasis," *Nat. Immunol.*, (2010), vol. 11, pp. 785-797.

Ricklin, D., et al., "Complement-targeted therapeutics," *Nat. Biotechnol.*, (2007), vol. 25, pp. 1265-1275.

Sahu, A., et al., 2000, "Complement Inhibitors Targeting C3, C4, and C5," in *Contemporary Immunology: Therapeutic Interventions in the Complement System*, pp. 75-112, J.D. Lambris and V.M. Holers, Eds., Humana Press Inc., Totowa, NJ.

Schenkein, H.A., et al., "Gingival fluid and serum in periodontal diseases: II. Evidence for cleavage of complement components C3, C3 proactivator (Factor B) and C4 in gingival fluid," *J. Periodontol.*, (1977), vol. 48, pp. 778-784.

Serhan, C.N., et al., "Resolving inflammation: dual anti-inflammatory and pro-resolution lipid mediators," *Nat. Rev. Immunol.*, (2008), vol. 8, pp. 349-361.

Socransky, S.S., et al., "Microbial complexes in subgingival plaque, " *J. Clin. Periodontol.*, (1998), vol. 25, pp. 134-144.

Tonetti, M.S., et al., "Treatment of periodontitis and endothelial function," *New England J. Med.*, (2007), vol. 356, pp. 911-920.

Van Dyke, T.E., "The management of inflammation in periodontal disease," *J Periodontol.*, (2008), vol. 79 (8 Suppl), pp. 1601-1608.

International Search Report and Written Opinion in International Application No. PCT/US2013/046599, mailed Sep. 30, 2013.

Maekawa et al., "Genetic and Intervention Studies Implicating Complement C3 as a Major Target for the Treatment of Periodontitis," J. Immunol. 192(12):6020-6027 (2014).

Extended European Search Report and Opinion in European Patent Application No. 13807873.8, mailed Feb. 3, 2016.

\* cited by examiner

SEQUENCE LISTING

```
<160> NUMBER OF SEQ ID NOS: 31

<210> SEQ ID NO 1
<211> LENGTH: 13
<212> TYPE: PRT
<213> ORGANISM: Artificial Sequence
<220> FEATURE:
<223> OTHER INFORMATION: compstatin
<220> FEATURE:
<221> NAME/KEY: DISULFID
<222> LOCATION: (2)..(12)
<223> OTHER INFORMATION: Cysteines joined via disulfide bridge.

<400> SEQUENCE: 1

Ile Cys Val Val Gln Asp Trp Gly His His Arg Cys Thr
1               5                   10

<210> SEQ ID NO 2
<211> LENGTH: 11
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (1)..(11)
<223> OTHER INFORMATION: Cysteines joined via disulfide bridge.
```

```
<400> SEQUENCE: 2

Cys Val Val Gln Asp Trp Gly His His Arg Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (1)..(11)
<223> OTHER INFORMATION: Cysteines joined via disulfide bridge.

<400> SEQUENCE: 3

Cys Val Ala Gln Asp Trp Gly His His Arg Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (1)..(11)
<223> OTHER INFORMATION: Cysteines joined via disulfide bridge.

<400> SEQUENCE: 4

Cys Val Val Gln Asp Trp Gly Ala His Arg Cys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (1)..(11)
<223> OTHER INFORMATION: Cysteines joined via disulfide bridge.

<400> SEQUENCE: 5

Cys Val Val Gln Asp Trp Gly His Ala Arg Cys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (1)..(11)
<223> OTHER INFORMATION: Cysteines joined via disulfide bridge.

<400> SEQUENCE: 6

Cys Val Val Gln Asp Trp Gly His His Ala Cys
1               5                   10

<210> SEQ ID NO 7
<211> LENGTH: 13
<212> TYPE: PRT
<213> ORGANISM: Artificial Sequence
<220> FEATURE:
```

```
<223> OTHER INFORMATION: compstatin-amidation
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (13)..(13)
<223> OTHER INFORMATION: AMIDATION

<400> SEQUENCE: 7

Ile Cys Val Val Gln Asp Trp Gly His His Arg Cys Thr
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (13)..(13)
<223> OTHER INFORMATION: AMIDATION

<400> SEQUENCE: 8

Ile Cys Val Trp Gln Asp Trp Gly Ala His Arg Cys Thr
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: MOD_RES
<222> LOCATION: (13)..(13)
<223> OTHER INFORMATION: AMIDATION

<400> SEQUENCE: 9

Ile Cys Val Trp Gln Asp Trp Gly Ala His Arg Cys Thr
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: compstatin analog (Cp10)
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: MOD_RES
<222> LOCATION: (8)..(8)
<223> OTHER INFORMATION: METHYLATION, MeGly
<220> FEATURE:
<221> NAME/KEY: MOD_RES
<222> LOCATION: (13)..(13)
<223> OTHER INFORMATION: AMIDATION

<400> SEQUENCE: 10

Ile Cys Val Trp Gln Asp Trp Gly Ala His Arg Cys Ile
1               5                   10

<210> SEQ ID NO 11
<211> LENGTH: 13
<212> TYPE: PRT
<213> ORGANISM: Artificial Sequence
<220> FEATURE:
<223> OTHER INFORMATION: compstatin analog (Cp20)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: MOD_RES
<222> LOCATION: (8)..(8)
<223> OTHER INFORMATION: METHYLATION, MeGly
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 11

Ile Cys Val Trp Gln Asp Trp Gly Ala His Arg Cys Ile
1               5                   10

<210> SEQ ID NO 12
<211> LENGTH: 13
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (4)..(4)
<223> OTHER INFORMATION: 1-methyl-tryptophan
```

```
<220> FEATURE:
<221> NAME/KEY: MOD_RES
<222> LOCATION: (8)..(8)
<223> OTHER INFORMATION: METHYLATION, MeGly
<220> FEATURE:
<221> NAME/KEY: MOD_RES
<222> LOCATION: (13)..(13)
<223> OTHER INFORMATION: AMIDATION
<220> FEATURE:
<221> NAME/KEY: MOD_RES
<222> LOCATION: (13)..(13)
<223> OTHER INFORMATION: METHYLATION

<400> SEQUENCE: 12

Ile Cys Val Trp Gln Asp Trp Gly Ala His Arg Cys Ile
1               5                   10

<210> SEQ ID NO 13
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 13

Gly Ile Cys Val Trp Gln Asp Trp Gly Ala His Arg Cys Ile
1               5                   10

<210> SEQ ID NO 14
<211> LENGTH: 14
<212> TYPE: PRT
<213> ORGANISM: Artificial Sequence
<220> FEATURE:
<223> OTHER INFORMATION: compstatin analog (Cp30)
<220> FEATURE:
<221> NAME/KEY: MOD_RES
<222> LOCATION: (1)..(1)
<223> OTHER INFORMATION: METHYLATION, MeGly
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
```

```
<221> NAME/KEY: MOD_RES
<222> LOCATION: (14)..(14)
<223> OTHER INFORMATION: AMIDATION

<400> SEQUENCE: 14

Gly Ile Cys Val Trp Gln Asp Trp Gly Ala His Arg Cys Ile
1               5                   10

<210> SEQ ID NO 15
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 15

Tyr Ile Cys Val Trp Gln Asp Trp Gly Ala His Arg Cys Ile
1               5                   10

<210> SEQ ID NO 16
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 16

Phe Ile Cys Val Trp Gln Asp Trp Gly Ala His Arg Cys Ile
1               5                   10

<210> SEQ ID NO 17
<211> LENGTH: 14
<212> TYPE: PRT
```

```
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 17

Arg Ile Cys Val Trp Gln Asp Trp Gly Ala His Arg Cys Ile
1               5                   10

<210> SEQ ID NO 18
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 18

Trp Ile Cys Val Trp Gln Asp Trp Gly Ala His Arg Cys Ile
1               5                   10

<210> SEQ ID NO 19
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
```

<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 19

Thr Ile Cys Val Trp Gln Asp Trp Gly Ala His Arg Cys Ile
1               5                   10

<210> SEQ ID NO 20
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: O-methyl-L-tyrosine
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 20

Tyr Ile Cys Val Trp Gln Asp Trp Gly Ala His Arg Cys Ile
1               5                   10

<210> SEQ ID NO 21
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)

```
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 21

Phe Ile Cys Val Trp Gln Asp Trp Gly Ala His Arg Cys Ile
1               5                   10

<210> SEQ ID NO 22
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 22

Val Ile Cys Val Trp Gln Asp Trp Gly Ala His Arg Cys Ile
1               5                   10

<210> SEQ ID NO 23
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION
```

<400> SEQUENCE: 23

Ile Ile Cys Val Trp Gln Asp Trp Gly Ala His Arg Cys Ile
1               5                   10

<210> SEQ ID NO 24
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 24

Ala Ile Cys Val Trp Gln Asp Trp Gly Ala His Arg Cys Ile
1               5                   10

<210> SEQ ID NO 25
<211> LENGTH: 14
<212> TYPE: PRT
<213> ORGANISM: Artificial Sequence
<220> FEATURE:
<223> OTHER INFORMATION: compstatin analog (Cp40)
<220> FEATURE:
<221> NAME/KEY: MOD_RES
<222> LOCATION: (1)..(1)
<223> OTHER INFORMATION: D-Tyrosine
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 25

Tyr Ile Cys Val Trp Gln Asp Trp Gly Ala His Arg Cys Ile
1               5                   10

```
<210> SEQ ID NO 26
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 26

Phe Ile Cys Val Trp Gln Asp Trp Gly Ala His Arg Cys Ile
1               5                   10

<210> SEQ ID NO 27
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: D-tryptophan
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 27

Trp Ile Cys Val Trp Gln Asp Trp Gly Ala His Arg Cys Ile
1               5                   10

<210> SEQ ID NO 28
<211> LENGTH: 14
<212> TYPE: PRT
```

```
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: D-cyclohexylalanine
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 28

Ala Ile Cys Val Trp Gln Asp Trp Gly Ala His Arg Cys Ile
1               5                   10

<210> SEQ ID NO 29
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
<222> LOCATION: (1)..(1)
<223> OTHER INFORMATION: D-alanine
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 29

Ala Ile Cys Val Trp Gln Asp Trp Gly Ala His Arg Cys Ile
1               5                   10

<210> SEQ ID NO 30
<211> LENGTH: 13
<212> TYPE: PRT
<213> ORGANISM: Artificial Sequence
<220> FEATURE:
<223> OTHER INFORMATION: compstatin analog
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: DISULFID
<222> LOCATION: (2)..(12)
<223> OTHER INFORMATION: Cysteines joined via disulfide bridge.
<220> FEATURE:
<221> NAME/KEY: MOD_RES
<222> LOCATION: (4)..(4)
<223> OTHER INFORMATION: 1-methyl-tryptophan
<220> FEATURE:
<221> NAME/KEY: MOD_RES
<222> LOCATION: (8)..(8)
<223> OTHER INFORMATION: METHYLATION, MeGly
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 30

Trp Cys Val Trp Gln Asp Trp Gly Ala His Arg Cys Ile
1               5                   10

<210> SEQ ID NO 31
<211> LENGTH: 14
<212> TYPE: PRT
<213> ORGANISM: Artificial Sequence
<220> FEATURE:
<223> OTHER INFORMATION: compstatin analog
<220> FEATURE:
<221> NAME/KEY: DISULFID
<222> LOCATION: (3)..(13)
<223> OTHER INFORMATION: Cysteines joined via disulfide bridge.
<220> FEATURE:
<221> NAME/KEY: MOD_RES
<222> LOCATION: (5)..(5)
<223> OTHER INFORMATION: 1-methyl-tryptophan
<220> FEATURE:
<221> NAME/KEY: MOD_RES
<222> LOCATION: (9)..(9)
<223> OTHER INFORMATION: METHYLATION, MeGly
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 31

Tyr Gly Cys Val Trp Gln Asp Trp Gly Ala His Arg Cys Ile
1               5                   10
```

METHODS OF TREATING OR PREVENTING PERIODONTITIS AND DISEASES ASSOCIATED WITH PERIODONTITIS

CROSS-REFERENCE TO RELATED APPLICATIONS

This application claims benefit under 35 U.S.C. 119(e) to U.S. Application No. 61/662,022 filed Jun. 20, 2012.

FEDERALLY SPONSORED RESEARCH OR DEVELOPMENT

This invention was made with government support under Grant No. DE021685 awarded by National Institute of Dental and Craniofacial Research (NIDCR), a National Institutes of Health. The government has certain rights in the invention.

TECHNICAL FIELD

This disclosure generally relates to periodontal disease and methods of treating or preventing periodontitis.

BACKGROUND

Periodontitis is a prevalent chronic inflammatory disease that leads to the destruction of the tissues that surround and support the teeth (periodontium). This oral disease is initiated by bacterial biofilms, which form on subgingival tooth surfaces and comprise mostly communities of gram-negative anaerobic species. The host inflammatory response to chronic microbial challenge at the dentogingival niche is implicated in inflicting damage upon the periodontium.

Although traditionally perceived as an antimicrobial enzyme system in serum, complement is now recognized as a central component of host defense impacting both innate and adaptive immunity. Not surprisingly, given its importance in fighting pathogens, complement constitutes a key target of immune evasion by microbes that cause persistent infections.

SUMMARY

The present disclosure describes methods for preventing or treating periodontitis or diseases associated with periodontitis. The present disclosure also describes methods of screening for compounds that can be used to prevent or treat periodontitis or diseases associated with periodontitis.

In one aspect, a method of treating or preventing periodontitis or diseases associated with periodontitis in an individual is provided. Such a method generally includes administering a compound to the individual that inhibits or blocks C3 expression, activity, or activation. Representative compounds include, without limitation, compstatin, analogs of compstatin, complement receptor 1-related gene/protein y (Crry), and complement activation blocker-2. Another representative compound is an antibody against C3, or, for example, a peptidomimetic antagonist of C3. Representative diseases associated with periodontitis include, without limitation, atherosclerosis, diabetes, osteoporosis, and pre-term labor.

In another aspect, a method of reducing the amount of *Porphyromonas gingivalis* and/or the inflammation caused by *P. gingivital* in an individual is provided. Such a method generally includes administering, to the individual, a compound that inhibits or blocks C3 expression, activity, or activation. Representative compounds include, without limitation, compstatin, analogs of compstatin, complement receptor 1-related gene/protein y (Crry), and complement activation blocker-2.

In still another aspect, a method of screening for compounds that treat or prevent periodontitis or diseases associated with periodontitis is provided. Such a method typically includes contacting a cell, in the presence of *P. gingivalis*, with a test compound; and evaluating the cell for expression, activity, or activation of C3. Generally, a reduction in the expression, activity, or activation of C3 in the presence of a test compound is indicative of a test compound that can be used to treat or prevent periodontitis or diseases associated with periodontitis. In some embodiments, the cell is a mammalian cell. In some embodiments, the cell is a recombinant cell comprising an exogenous nucleic acid encoding C3.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1 is graphs showing that C3 deficiency protects against inflammatory periodontal bone loss.

FIGS. 4A, 4B, 4C, and 4D show results for probing pocket depth, gingival index, bleeding on probing, and mobility index, respectively, which are measurements typically used to detect clinical periodontal inflammation and bone lose. FIG. 4E represents a radiograph measurement of bone height. Starting 3 days after initiation of ligature-induced periodontitis, Cp40 (500 µg) was injected locally into the maxillary interdental papillae from the $1^{st}$ premolar to the $2^{nd}$ molar, in two animals, three times weekly. An inactive analog of Cp40 (control) was injected into the contralateral side of the mouth in the same two animals (split-mouth design). Shown are the effects of Cp40 on the indicated inflammatory clinical parameters and bone heights, determined using standardized X-ray images (taken at week 6) and NIKON imaging system software. Specifically, the distance between the cement-enamel junction (CEJ) and alveolar bone crest (ABC) was measured at six points ($1^{st}$ premolar, distal; $2^{nd}$ premolar mesial & distal; $1^{st}$ molar, mesial & distal; $2^{nd}$ molar mesial) and the data in Panel E reflect the 6-site total. The higher CEJ-ABC distance values of the controls as compared to those of Cp40 treatments signify increased bone loss in the absence of drug treatment. In all animals, the gingival margin was at the cement-enamel junction, and thus, PPD readings equaled clinical attachment loss (CAL).

FIG. 5E), and osteoprotegerin (OPG; FIG. 5F). At the same timepoints that clinical exams were performed (as per FIG. 4), GCF was collected from the same monkeys (treatment details in FIG. 4 legend) using PERIOPAPER absorbent strips to assay the indicated cytokines. Total cytokine content in the eluted GCF samples was measured using MILLIPLEX MAP (multi-analyte panels) kits on a BIO-PLEX detection system. In Panel G, TRAP-positive multinucleated cells (osteoclasts) were enumerated in nine serial sections for each bone biopsy specimen taken between the $2^{nd}$ premolar and $1^{st}$ molar of each animal.

Like reference symbols in the various drawings indicate like elements.

BRIEF DESCRIPTION OF THE BIOLOGICAL SEQUENCES

Figure 1A:
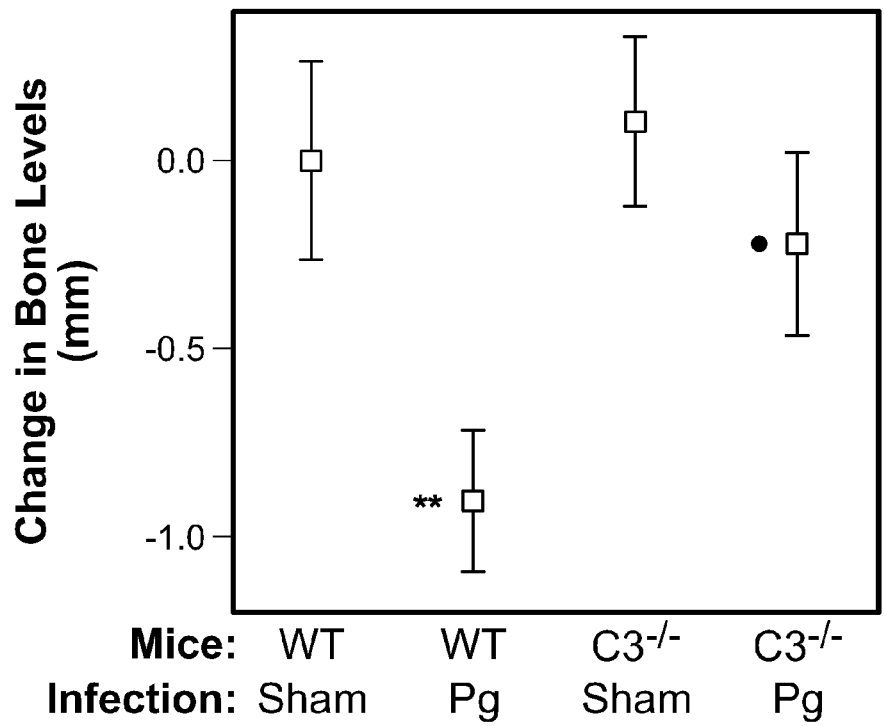
FIG. 1A is a graph showing periodontal bone levels.

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for amino acid sequence data comply with the rules set forth in 37 C.F.R. §1.822.

The amino acid sequences for Compstatin and analogs of Compstatin are depicted in Table A.

TABLE A

Compstatin and Compstatin analogs.

| Peptide Name | Amino Acid Sequence | SEQ ID NO. |
| --- | --- | --- |
| Compstatin | Ile-Cys*-Val-Val-Gln-Asp-Trp-Gly-His-His-Arg-Cys*-Thr | SEQ ID NO: 1 |
| Peptide VI | Cys*-Val-Val-Gln-Asp-Trp-Gly-His-His-Arg-Cys* | SEQ ID NO: 2 |
| Peptide VIII | Cys*-Val-Ala-Gln-Asp-Trp-Gly-His-His-Arg-Cys* | SEQ ID NO: 3 |
| Peptide XIII | Cys*-Val-Val-Gln-Asp-Trp-Gly-Ala-His-Arg-Cys* | SEQ ID NO: 4 |
| Peptide XIV | Cys*-Val-Val-Gln-Asp-Trp-Gly-His-Ala-Arg-Cys* | SEQ ID NO: 5 |
| Peptide XV | Cys*-Val-Val-Gln-Asp-Trp-Gly-His-His-Ala-Cys* | SEQ ID NO: 6 |
| Compstatin-NH$_2$ | Ile-Cys*-Val-Val-Gln-Asp-Trp-Gly-His-His-Arg-Cys*-Thr-NH$_2$ | SEQ ID NO: 7 |
| 4W9A | Ac-Ile-Cys*-Val-Trp-Gln-Asp-Trp-Gly-Ala-His-Arg-Cys*-Thr-NH$_2$ | SEQ ID NO: 8 |
| 4(1MeW) | Ac-Ile-Cys*-Val-Trp(1Me)-Gln-Asp-Trp-Gly-Ala-His-Arg-Cys*-Thr-NH$_2$ | SEQ ID NO: 9 |
| Cp10 | Ac-Ile-Cys*-Val-Trp(1Me)-Gln-Asp-Trp-Sar-Ala-His-Arg-Cys*-Ile-NH$_2$ | SEQ ID NO: 10 |
| Cp20 | Ac-Ile-Cys*-Val-Trp(1Me)-Gln-Asp-Trp-Sar-Ala-His-Arg-Cys*-mIle-NH$_2$ | SEQ ID NO: 11 |
| Peptide 1 | Me-Ile-Cys*-Val-Trp(1Me)-Gln-Asp-Trp-Sar-Ala-His-Arg-Cys*-mIle-NH$_2$ | SEQ ID NO: 12 |
| Peptide 2 | Gly-Ile-Cys*-Val-Trp(1Me)-Gln-Asp-Trp-Sar-Ala-His-Arg-Cys*-mIle-NH$_2$ | SEQ ID NO: 13 |
| Peptide 3 (Cp30) | Sar-Ile-Cys*-Val-Trp(1Me)-Gln-Asp-Trp-Sar-Ala-His-Arg-Cys*-mIle-NH$_2$ | SEQ ID NO: 14 |
| Peptide 4 | Tyr-Ile-Cys*-Val-Trp(1Me)-Gln-Asp-Trp-Sar-Ala-His-Arg-Cys*-mIle-NH$_2$ | SEQ ID NO: 15 |
| Peptide 5 | Phe-Ile-Cys*-Val-Trp(1Me)-Gln-Asp-Trp-Sar-Ala-His-Arg-Cys*-mIle-NH$_2$ | SEQ ID NO: 16 |
| Peptide 6 | Arg-Ile-Cys*-Val-Trp(1Me)-Gln-Asp-Trp-Sar-Ala-His-Arg-Cys*-mIle-NH$_2$ | SEQ ID NO: 17 |

TABLE A-continued

Compstatin and Compstatin analogs.

| Peptide Name | Amino Acid Sequence | SEQ ID NO. |
|---|---|---|
| Peptide 7 | Trp-Ile-Cys*-Val-Trp(1Me)-Gln-Asp-Trp-Sar-Ala-His-Arg-Cys*-mIle-NH$_2$ | SEQ ID NO: 18 |
| Peptide 8 | Thr-Ile-Cys*-Val-Trp(1Me)-Gln-Asp-Trp-Sar-Ala-His-Arg-Cys*-mIle-NH$_2$ | SEQ ID NO: 19 |
| Peptide 9 | Tyr(Me)-Ile-Cys*-Val-Trp(1Me)-Gln-Asp-Trp-Sar-Ala-His-Arg-Cys*-mIle-NH$_2$ | SEQ ID NO: 20 |
| Peptide 10 | mPhe-Ile-Cys*-Val-Trp(1Me)-Gln-Asp-Trp-Sar-Ala-His-Arg-Cys*-mIle-NH$_2$ | SEQ ID NO: 21 |
| Peptide 11 | mVal-Ile-Cys*-Val-Trp(1Me)-Gln-Asp-Trp-Sar-Ala-His-Arg-Cys*-mIle-NH$_2$ | SEQ ID NO: 22 |
| Peptide 12 | mIle-Ile-Cys*-Val-Trp(1Me)-Gln-Asp-Trp-Sar-Ala-His-Arg-Cys*-mIle-NH$_2$ | SEQ ID NO: 23 |
| Peptide 13 | mAla-Ile-Cys*-Val-Trp(1Me)-Gln-Asp-Trp-Sar-Ala-His-Arg-Cys*-mIle-NH$_2$ | SEQ ID NO: 24 |
| Peptide 14 (Cp40) | dTyr-Ile-Cys*-Val-Trp(1Me)-Gln-Asp-Trp-Sar-Ala-His-Arg-Cys*-mIle-NH$_2$ | SEQ ID NO: 25 |
| Peptide 15 | dPhe-Ile-Cys*-Val-Trp(1Me)-Gln-Asp-Trp-Sar-Ala-His-Arg-Cys*-mIle-NH$_2$ | SEQ ID NO: 26 |
| Peptide 16 | dTrp-Ile-Cys*-Val-Trp(1Me)-Gln-Asp-Trp-Sar-Ala-His-Arg-Cys*-mIle-NH$_2$ | SEQ ID NO: 27 |
| Peptide 17 | dCha-Ile-Cys*-Val-Trp(1Me)-Gln-Asp-Trp-Sar-Ala-His-Arg-Cys*-mIle-NH$_2$ | SEQ ID NO: 28 |
| Peptide 18 | dAla-Ile-Cys*-Val-Trp(1Me)-Gln-Asp-Trp-Sar-Ala-His-Arg-Cys*-mIle-NH$_2$ | SEQ ID NO: 29 |
| Peptide 19 | Ac-Trp-Cys*-Val-Trp(1Me)-Gln-Asp-Trp-Sar-Ala-His-Arg-Cys*-mIle-NH$_2$ | SEQ ID NO: 30 |
| Peptide 20 | Tyr-Gly-Cys*-Val-Trp(1Me)-Gln-Asp-Trp-Sar-Ala-His-Arg-Cys*-mIle-NH$_2$ | SEQ ID NO: 31 |

Cys* = oxidized cystein residues optionally joined together via a disulfide bridge.
NH$_2$ = amidation of the C-terminus.
Ac = acetylation of the N-terminus.
Trp(1Me) = 1-methyl-trptophan.
Sar = sarcosine (N-methyl-glycine).
Me = methylation of the N-terminus.
m = methylated amino acid residue.
Tyr(Me) = 0-methyl-L-tyrosine.
d = D-stereoisomer of an amino acid residue.
Cha = cyclohexylalanine.

DETAILED DESCRIPTION

Periodontitis is a set of inflammatory diseases affecting the periodontium, i.e., the tissues that surround and support the teeth. Periodontitis involves progressive loss of the alveolar bone around the teeth, and, if left untreated, can lead to the loosening and subsequent loss of teeth. Periodontitis is caused by microorganisms that adhere to and grow on the tooth's surfaces, along with an overly aggressive immune response against these microorganisms. Periodontitis manifests as painful, red, swollen gums, with abundant plaque. Symptoms may include redness or bleeding of gums while brushing teeth, using dental floss, or biting into hard food (e.g. apples); recurrent swelling of the gum; halitosis and a persistent metallic taste in the mouth; gingival recession resulting in apparent lengthening of teeth; deep pockets between the teeth and the gums (pockets are sites where the attachment has been gradually destroyed by collagenases); and loose teeth.

In 1999, a classification system was developed for periodontal diseases and conditions, which listed seven major categories of periodontal diseases, of which the last six are termed "destructive periodontal disease" because they are essentially irreversible. In addition, terminology expressing both the extent and severity of periodontal diseases are appended to the classes to further denote the specific diagnosis. The extent of disease refers to the proportion of the dentition affected by the disease in terms of percentage of sites. Sites are defined as the positions at which probing measurements are taken around each tooth and, generally, six probing sites around each tooth are recorded to make a determination of the extent of periodontal disease. Typically, if up to 30% of sites in the mouth are affected, the manifestation is classification as localized; if more than 30% of sites in the mouth are affected, the term generalized is used. The severity of disease refers to the amount of periodontal ligament fibers that have been lost, termed clinical attachment loss, and is defined by the American Academy of Periodontology as mild (1-2 mm of attachment loss), moderate (3-4 mm of attachment loss), or severe (≥5 mm of attachment loss).

Periodontitis also has been shown to have effects outside of the mouth. For example, periodontitis has been linked to increased inflammation as indicated by increased levels of C-reactive protein and Interleukin-6 (IL-6). In addition, periodontitis has been shown to increase the risk for a number of other diseases, including but not limited to, stroke, myocardial infarction, atherosclerosis, diabetes, osteoporosis, and pre-term labor.

The primary pathogen involved in periodontitis is *Porphyromonas gingivalis*, a gram-negative anaerobic bacterium. *P. gingivalis* inhibits the complement cascade, which usually converges at the third complement component (C3) and leads to the generation of effector molecules that mediate recruitment and activation of inflammatory cells via the anaphylatoxins, C3a and C5a, microbial opsonization and phagocytosis via opsonins such as C3b, and direct lysis of targeted microbes via the C5b-9 membrane attack complex.

Currently, there is no satisfactory adjunctive therapy in periodontitis; antimicrobials and antibiotics have largely failed in that regard. At present, perhaps the most promising approach is the use of agents that promote the resolution of inflammation (e.g., lipoxins and resolvins), although at least some of these agents appear to have stability issues (e.g., easily becomes oxidized and loses biological activity).

Methods of Treating or Preventing Periodontitis or Diseases Associated with Periodontitis The mechanisms used by *P. gingivalis* to overcome and thwart the host's immune response as described herein can be used against the pathogen in methods of treating or preventing periodontitis or diseases associated with periodontitis. For example, blocking C3 effectively deprives *P. gingivalis* of crucial survival tactics. Thus, methods that inhibit or block C3 expression, activity or activation can be used to reduce the amount of *P. gingivalis* in an individual, thereby protecting the individual from periodontitis and associated systemic diseases like atherosclerosis. In addition, methods that inhibit the immunosuppressive signaling that occurs in the presence of C3 also can be used to reduce the amount of *P. gingivalis* in an individual, thereby protecting the individual from periodontitis and associated systemic diseases.

Such methods (e.g., methods of inhibiting or blocking C3 expression, activity or activation) typically include administering a compound to the individual that inhibits or blocks C3 expression, activity or activation. By way of example, there are a number of compounds that are known to inhibit or block C3 expression, activity, or activation (e.g., C3 antagonists). For example, compstatin or analogs of compstatin, complement receptor 1-related gene/protein y (Crry), and complement activation blocker-2 are inhibitors of C3 that are known in the art. See, for example, Sahu et al., 2000, "Complement Inhibitors Targeting C3, C4, and C5", in *Contemporary Immunology: Therapeutic Interventions in the Complement System*, pp. 75-112, Lambris and Holers, Eds., Humana Press Inc., Totowa, N.J.; and Qu et al., 2012, "New analogs of the clinical complement inhibitor compstatin with subnanomolar affinity and enhanced pharmacokinetic properties," Immunobiology, 218:496-505. The compstatin and compstatin analog sequences disclosed in the foregoing references are summarized in Table A above.

An antibody against C3 also can be used to inhibit or block C3 expression, activity, or activation. Antibodies against C3 are known and are commercially available from, for example, CREATIVE BIOMART (Shirley, N.Y.), ABCAM (Cambridge, Mass.), and ACRIS ANTIBODIES (San Diego, Calif.). In addition, RNA interference ("RNAi") can be used to specifically target the nucleic acid encoding C3. RNAi is a process that is used to induce specific post-translational gene silencing. RNAi involves introduction of RNA with partial or fully double-stranded character into the cell or into the extracellular environment. The portion of the target gene used to make RNAi can encompass exons but also can include untranslated regions (UTRs) as well as introns. See, for example, Kim et al., 2008, Biotechniques, 44:613-6 as well as Lares et al., 2010, *Trends Biotechnol.*, 28:570-9; and Pfeifer et al., 2010, *Pharmacol. Ther,* 126:217-27. See, also, Ricklin & Lambris, 2007, *Nature Biotechnol.*, 25:1265-75.

In certain embodiments, one or more inhibitors of complement can be administered to an individual and used to prevent or treat periodontitis (or diseases associated with periodontitis) via the role of complement, as described herein, in the formation of periodontitis and, specifically, in the establishment of *P. gingivalis*. Representative complement inhibitors include, without limitation, sCR1, C1 Inhibitor (C1inh), Membrane Cofactor Protein (MCP), Decay Accelerating Factor (DAF), MCP-DAF fusion protein (CAB-2), C4 bp, Factor H, Factor I, Carboxypeptidase N, vitronectin (S Protein), clusterin, CD59, compstatin and its functional analogs, C1q inhibitors or anti-C1q antibodies, C1 inhibitors or anti-C1 antibodies, C1r inhibitors or anti-C1r antibodies, C1s inhibitors or anti-Cis antibodies, MSP inhibitors or anti-MASP antibodies, MBL inhibitors or anti-MBL antibodies, C2 inhibitors or anti-C2 antibodies, C4 inhibitors or anti-C4 antibodies, C4a inhibitors or anti-C4a antibodies, C5 inhibitors or anti-CS antibodies, C5a inhibitors or anti-C5a antibodies, C5aR inhibitors or anti-C5aR antibodies, C5b inhibitors or anti-C5b antibodies, C3a inhibitors or anti-C3a antibodies, C3aR inhibitors or anti-C3aR antibodies, C6 inhibitors or anti-C6 antibodies, C7 inhibitors or anti-C7 antibodies, C8 inhibitors or anti-C8 antibodies, C9 inhibitors or anti-C9 antibodies, properdin inhibitors or anti-properdin antibodies, Factor B inhibitors or anti-Factor B antibodies, or Factor D inhibitors or anti-Factor D antibodies.

Compounds that inhibit or block C3 expression, activity, or activation can be administered to an individual via any number of routes, which typically depends on the particular compound and its features. Compounds can be incorporated into pharmaceutical compositions suitable for administration to an individual. Such compositions typically include, at least, the compound and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Additional or secondary active compounds also can be incorporated into the compositions described herein.

A pharmaceutical composition as described herein is formulated to be compatible with its intended route of administration. Examples of routes of administration include parenteral, e.g., intravenous, intradermal, subcutaneous, oral (e.g., ingestion or inhalation), transdermal (topical), transmucosal, and rectal administration. In addition, local administration into the periodontal pocket (e.g., via direct injection, or via, for example, a PERIOCHIP biodegradable chip) also is a route of administration that may be employed in the methods described herein. Solutions or suspensions used for parenteral, intradermal, or subcutaneous application can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and/or antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and/or by the use of surfactants. In many cases, it will be preferable to include isotonic agents, for example, sugars, polyalcohols such as mannitol or sorbitol, and sodium chloride in the composition. Prolonged administration of an injectable composition can be brought about by including an agent that delays absorption. Such agents include, for example, aluminum monostearate and gelatin. A parenteral preparation can be enclosed in ampoules, disposable syringes or multiple dose vials made of glass or plastic.

Oral compositions generally include an inert diluent or an edible carrier. Oral compositions can be liquid, or can be enclosed in gelatin capsules or compressed into tablets. Pharmaceutically compatible binding agents, and/or adjuvant materials can be included as part of an oral composition. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, PRIMOGEL (sodium carboxymethol cellulose), or corn starch; a lubricant such as magnesium stearate or Sterotes; a glidant such as colloidal silicon dioxide; a sweetening agent such as sucrose or saccharin; and/or a flavoring agent such as peppermint, methyl salicylate, or orange flavoring. Transmucosal administration can be accomplished through the use of nasal sprays or suppositories. For transdermal administration, the active compounds typically are formulated into ointments, salves, gels, or creams as generally known in the art.

It is especially advantageous to formulate oral or parenteral compositions in dosage unit form for ease of administration and uniformity of dosage. Dosage unit form as used herein refers to physically discrete units suited as unitary dosages for an individual to receive; each unit containing a predetermined quantity of active compound calculated to produce the desired therapeutic effect in association with the required pharmaceutical carrier. The dosage units themselves are dependent upon the amount of compound to be delivered. The amount of a compound necessary to inhibit or block C3 expression, activity or activation can be formulated in a single dose, or can be formulated in multiple dosage units. Treatment of an individual with a compound that inhibits or blocks C3 expression, activity or activation may require a one-time dose, or may require repeated or multiple doses.

Screening for Compounds that can be Used to Treat or Prevent Periodontitis or Diseases Associated with Periodontitis The results described herein regarding complement component C3 and *P. gingivalis* also can be used to screen for therapeutic compounds (i.e., compounds that inhibit the expression, activity, or activation of C3). For example, a nucleic acid molecule can be produced that includes a promoter operably linked to nucleic acid encoding a C3 polypeptide. Promoters that drive expression of a DNA sequence are well known in the art. Promoters suitable for expressing a nucleic acid encoding C3 are known to those skilled in the art and include, for example, constitutive or inducible promoters. Many constitutive and inducible promoters are known in the art. As used herein, "operably linked" means that a promoter and/or other regulatory element(s) are positioned in a vector relative to a nucleic acid encoding C3 in such a way as to direct or regulate expression of the nucleic acid. Such a nucleic acid molecule can be introduced into host cells (e.g., *E. coli*, yeast) using routine methods (e.g., electroporation, lipid-based delivery systems, nanoparticle delivery systems, and viral-based delivery systems), and the host cells can be contacted with a test compound. A vector as described herein also may include sequences such as those encoding a selectable marker (e.g., an antibiotic resistance gene).

Methods of evaluating whether or not a test compound inhibits the expression of C3 are well known in the art. For example, RT-PCR or Northern blotting methods can be used to determine the amount of C3 mRNA in the presence and absence of the test compound. In addition, methods that can be used to evaluate whether or not a test compound inhibits the activity or the activation of C3 are known in the art.

Methods of making recombinant host cells (e.g., recombinant mammalian host cells) are discussed herein and are well known in the art. In addition, virtually any type of compound can be used as a test compound in the screening methods described herein. Test compounds can include, for example and without limitation, nucleic acids, peptides, proteins, non-peptide compounds, synthetic compounds, peptidomimetics, antibodies, small molecules, fermentation products, or extracts (e.g., cell extracts, plant extracts, or animal tissue extracts).

In accordance with the present disclosure, there may be employed conventional molecular biology, microbiology, biochemical, and recombinant DNA techniques within the skill of the art. Such techniques are explained fully in the literature. The discovery will be further described in the following examples, which do not limit the scope of the methods and compositions of matter described in the claims.

EXAMPLES

Example 1

Mice Lacking C3 are Protected Against *P. gingivalis*-Induced Bone Loss

Figure 1B:
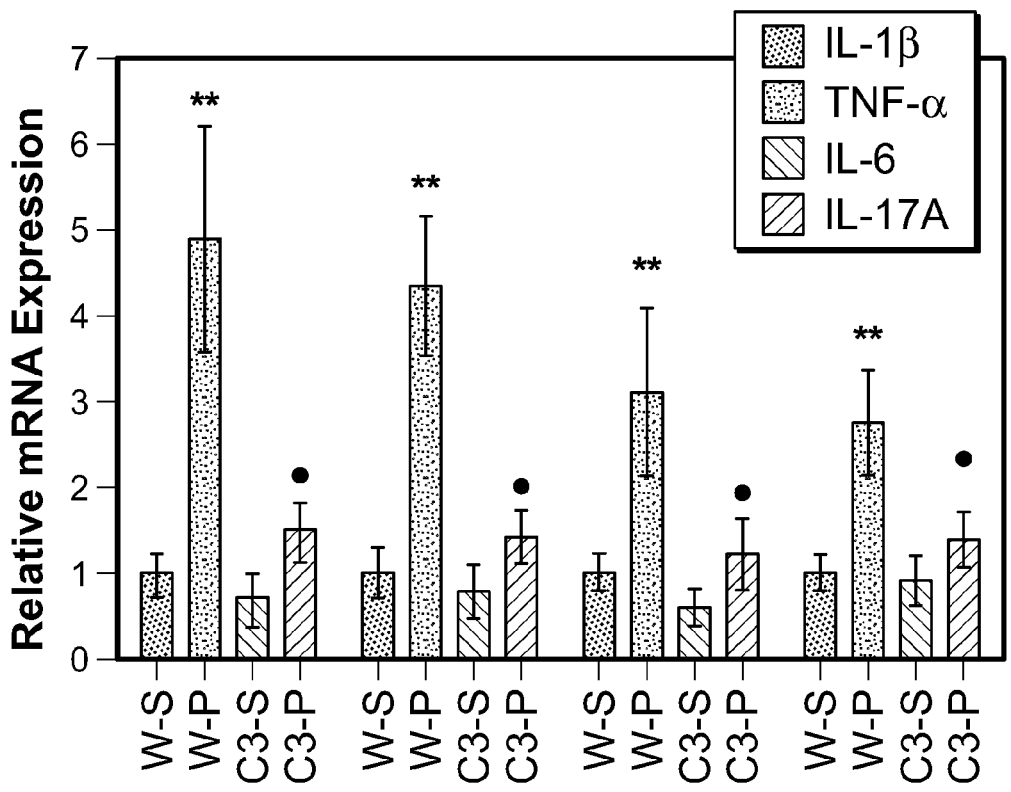
FIG. 1B reveals relative mRNA expression levels for the cytokines interleukin-1 beta (IL-1β), tumor necrosis factor alpha (TNF-α), interleukin 6 (IL-6), and interleukin 17A (IL-17A).

CS7BL/6 wild-type (WT) mice or mice deficient in C3 ($C3^{-/-}$) were orally infected or not with *P. gingivalis* (Pg) and assessed for induction of periodontal bone loss using defleshed maxillae (FIG. 1A). Buccal and lingual gingiva around the six maxilary molars were dissected from the same mice and processed for real-time PCR to determine mRNA expression levels for the indicated cytokines (normalized against GAPDH mRNA and expressed as fold induction relative to the sham-infected WT group) (FIG. 1B). Similar experiments were performed in which gingiva were homogenized and soluble extracts were used to determine cytokine levels using LUMINEX-100 immunoassay detection technology (FIG. 1C).

Figure 1C:
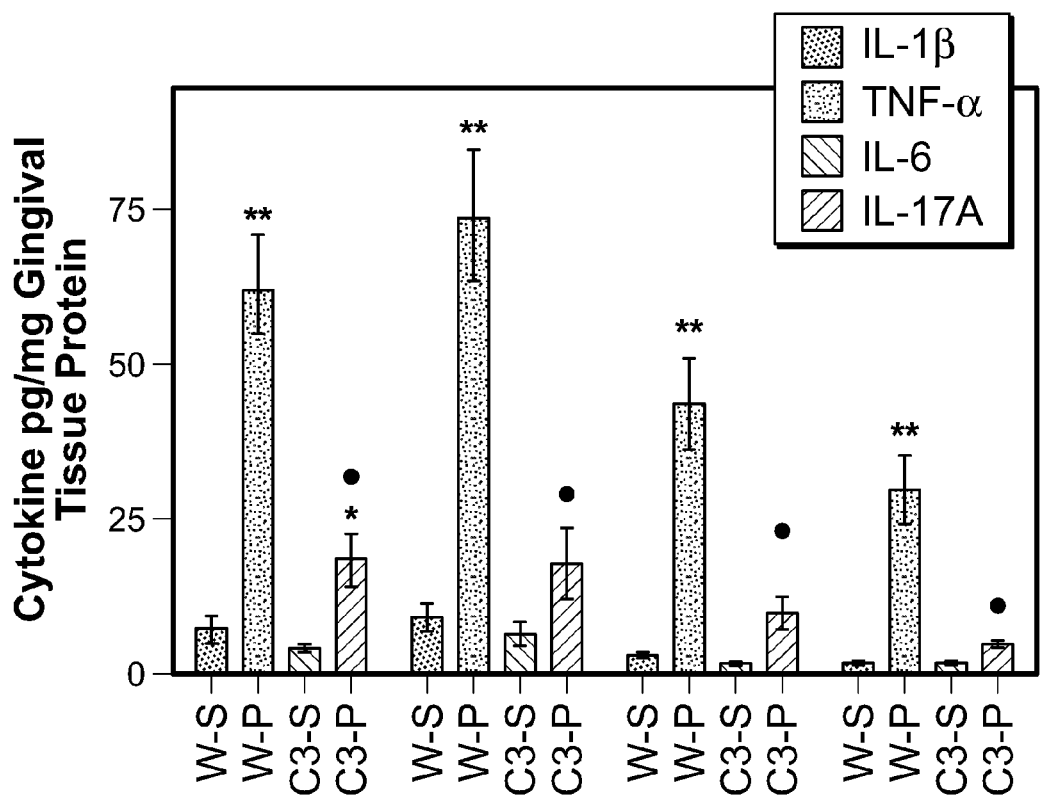
FIG. 1C demonstrates the protein levels of IL-1β, TNF-α, IL-6, and IL-17A in gingiva extract. Data are means±SD (n=5 mice). $P<0.05$ and **, $P<0.01$ vs. sham-infected WT, significant ($p<0.01$) inhibition of bone loss or cytokine induction. Key: W-S: WT & sham-infected; W-P: WT & Pg-infected; C3-S: C3−/− & sham-infected; C3-P: C3−/− & Pg-infected.

It was found that mice lacking the central complement component C3 ($C3^{-/-}$ mice) are protected against *Porphyromonas gingivalis*-induced bone loss relative to wild-type controls (FIG. 1). Inhibition of bone loss (FIG. 1A) correlated with diminished expression of inflammatory and bone resorptive cytokines (IL-1β, TNF-α, IL-6, and IL-17) at the mRNA (FIG. 1B) and protein (FIG. 1C) levels. These data conclusively implicate C3 in destructive periodontal inflammation.

Example 2

Colonization and Effects of *P. gingivalis* in the Periodontium of Normal or Complement-Deficient Mice Wild-type (WT) mice or mice deficient in C3 or C5aR were orally inoculated with *P. gingivalis* (Pg) or vehicle only (Sham) and were sacrificed 7 days later. The numbers of *P. gingivalis* and of total bacteria in the periodontal tissue were determined using quantitative real-time PCR of the ISPg1 gene (*P. gingivalis*) or the 16S rRNA gene (total bacteria).

Figure 2:
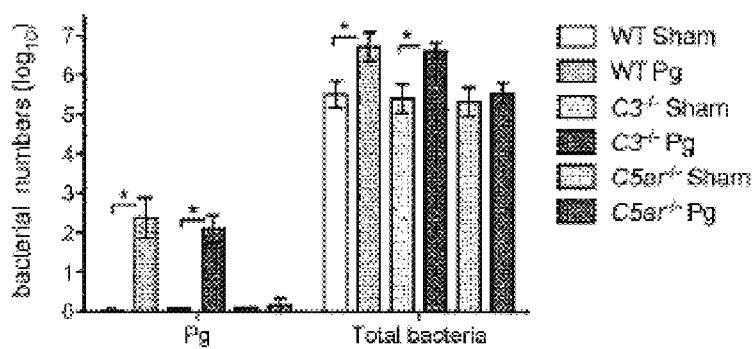
FIG. 2 is a graph showing the colonization and effects of *P. gingivalis* in the periodontium of normal or complement-deficient mice. Data are means±SD (n=5 mice per group). *$P<0.01$ between the indicated groups.

Whereas *P. gingivalis* cannot colonize the periodontium of CSaR-deficient mice ($C5ar^{-/-}$), it can colonize the periodontium of $C3^{-/-}$ mice and instigate an increase in the total bacterial counts, as it does in wild-type mice (FIG. 2). Taken together with the data shown in FIG. 1, these findings suggest that, whereas dysbiosis is necessary for inflammatory bone loss, it is not sufficient by itself. Rather, the dysbiotic microbiota requires the presence of C3 to induce maximum inflammation and bone loss.

Example 3

$C3^{-/-}$ Mice are Protected Against Ligature-Induced Periodontal Bone Loss

Bone loss was induced through the use of a 5-0 silk ligature tied around the maxillary second molar (L); the contralateral molar tooth in each mouse was left unligated as baseline control (UC or WT).

Figure 3:
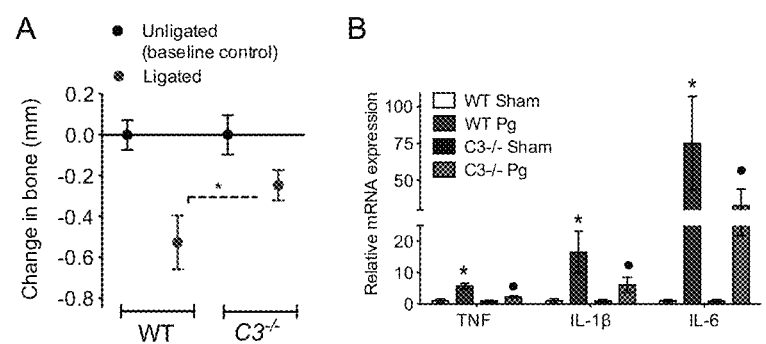
FIG. 3 are graphs showing bone loss measured in defleshed maxillae (Panel A) and mRNA expression of the indicated cytokines (normalized against GAPDH mRNA) and expressed as fold change in the transcript levels in the ligated site relative to those of the contralateral unligated site (assigned an average value of 1; Panel B). Data are means±SD (n=5 mice). Negative values indicate bone loss relative to the unligated contralateral tooth. *, $P<0.01$ vs. WT control. •, significant ($P<0.01$) inhibition of cytokine induction.

This results in a *P. gingivalis*-independent model of periodontitis, resulting in massive local accumulation of bacteria and rapid inflammatory bone loss. C3–/– mice were protected in this model based on bone loss (FIG. 3A) and mRNA expression of the indicated cytokines (FIG. 3B). Therefore, C3 is heavily involved in inflammatory bone loss suggesting that C3 inhibitors (e.g., compstatin) could find therapeutic application in periodontitis.

Example 4

Non-Human Primate Studies

The immune system and periodontal anatomy of the cynomolgus monkey is very similar to that of humans, and ligature-induced periodontitis in this NHP model displays bacteriological, immunohistological and clinical features that are most similar to those observed in human periodontitis. The cynomolgus monkey model is therefore considerably more predictive of drug efficacy in human periodontitis as compared to other, widely used preclinical animal models such as rodents. Moreover, the cynomolgus model of ligature-induced periodontitis allows longitudinal examination of the disease in a way that cannot be performed in humans.

Figure 4:
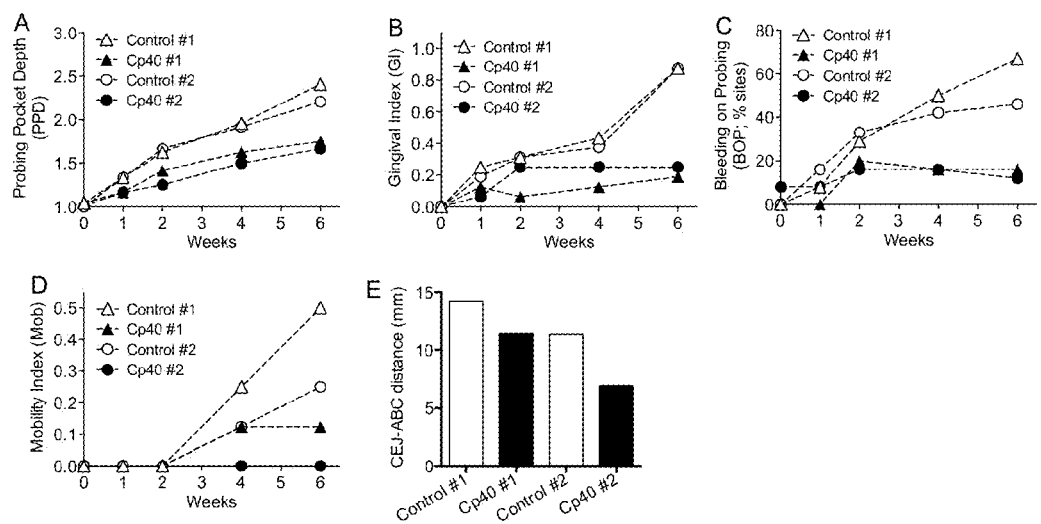
FIG. 4 are graphs showing that Cp40 decreases inflammatory clinical parameters of NHP periodontitis.
Figure 5:
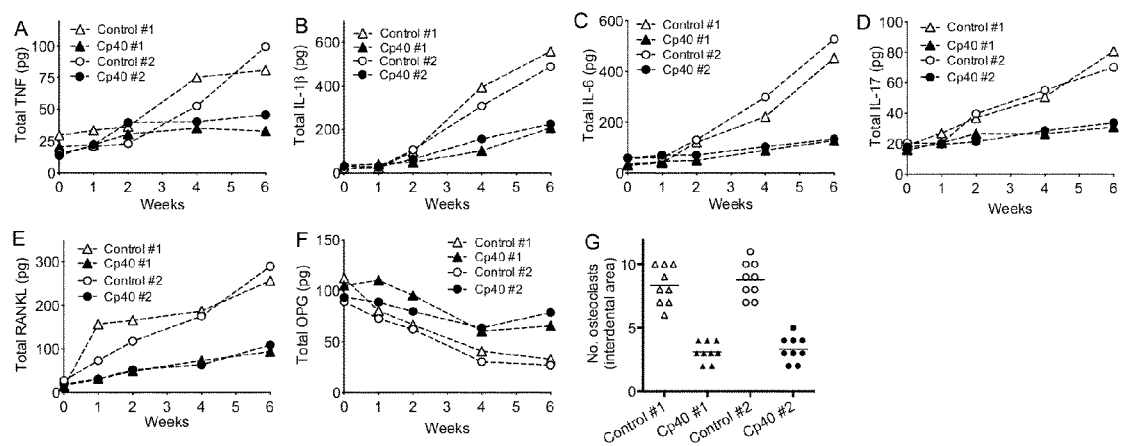
FIG. 5 are graphs showing that Cp40 inhibits proinflammatory cytokine production and osteoclastogenesis in NHP periodontitis. Specifically, the panels show the relative protein levels for TNF (FIG. 5A), IL-1b (FIG. 5B), IL-6 (FIG. 5C), IL-17A (FIG. 5D), receptor activator of nuclear factor kappa-B ligand (RANKL.

Silk ligatures were placed around maxillary posterior teeth ($2^{nd}$ premolar and $1^{st}$ molar) on both halves of the mouth for a split-mouth experimental design, i.e., one side was treated with active drug (Cp40, the current lead version of compstatin) and the other with inactive analog (control). Thus, each animal served as its own control. An initial study with a 6-week duration was conducted using two animals. Treatment with compstatin resulted in decreased clinical inflammation and bone loss (FIG. 4), as well as reduced levels of proinflammatory cytokines in the gingival crevicular fluid (GCF) and lower numbers of osteoclasts in bone biopsy specimens (FIG. 5), as compared to control treatments. Importantly, the decreased bone loss in sites treated with Cp40 (revealed radiographically by greater bone heights, i.e., CEJ-ABC distances; FIG. 4E) was consistent not only with decreased osteoclastogenesis (FIG. 5G) but also with decreased GCF levels of RANKL (FIG. 5E), a key osteoclasto-genic factor. Moreover, the GCF levels of osteoprotegerin (OPG), a natural inhibitor of RANKL, were maintained at higher levels in Cp40-treated sites than control sites during the course of the study (FIG. 5F).

Figure 6:
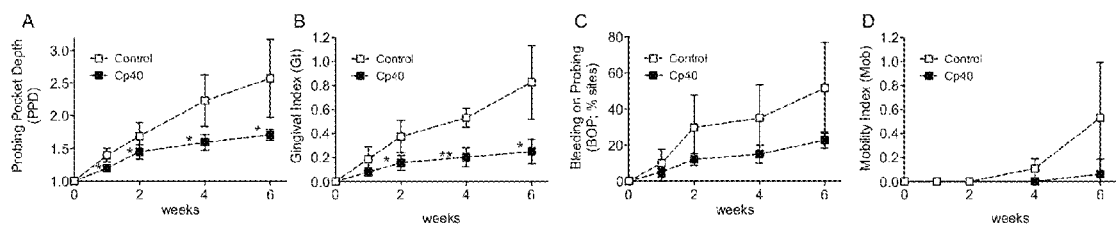
FIG. 6 are graphs showing a significant inhibition of inflammatory clinical parameters following treatment of NHP periodontitis with Cp40. Panels A, B, C, and D show measurements for probing pocket depth, gingival index, bleeding on probing, and mobility index, respectively, between Cp40 treated and control animals. Starting 3 days after initiation of ligature-induced periodontitis, Cp40 (500 µg) or control were injected locally into the mandibular interdental papillae from the $1^{st}$ premolar to the $2^{nd}$ molar, three times weekly, in opposites sides of the mouth (split-mouth design). The effects of Cp40 were determined on the indicated inflammatory clinical parameters at the indicated timepoints. In all animals, the gingival margin was at the cement-enamel junction, and thus, PPD readings equaled clinical attachment loss (CAL). Data are means±SD (n=4 monkeys). *, P<0.05; **, P<0.01 vs. control.
Figure 7:
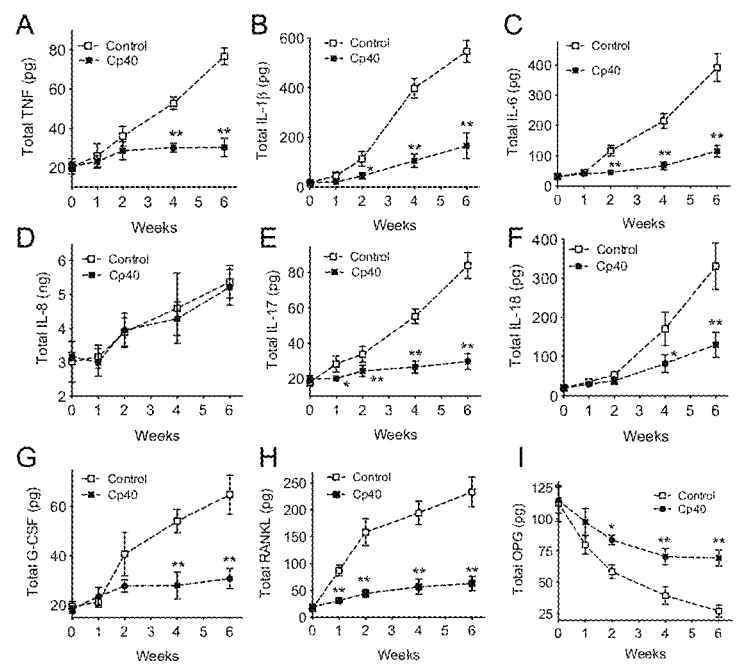
FIG. 7 are graphs showing decreased GCF levels of proinflammatory cytokines following treatment of NHP periodontitis with Cp40. Specifically, levels of TNF-α (Panel A), IL-1β (Panel B), IL-6 (Panel C), interleukin 8 (IL-8; Panel D), IL-17A (Panel E), interleukin 18 (IL-18; Panel F), granulocyte colony-stimulating factor (G-CSF; Panel G), RANKL (Panel H), and OPG (Panel I) were measured. At the same timepoints that clinical exams were performed (as per FIG. 6), GCF was collected from the same monkeys (treatment details in FIG. 6 legend) using PERIO-PAPER absorbent strips to assay the indicated cytokines. Total cytokine content in the eluted GCF samples was measured using MILLIPLEX MAP (multi-analyte panels) kits on a BIO-PLEX detection system. Data are means±SD (n=4 monkeys). *, P<0.05; **, P<0.01 vs. control.
Figure 8:
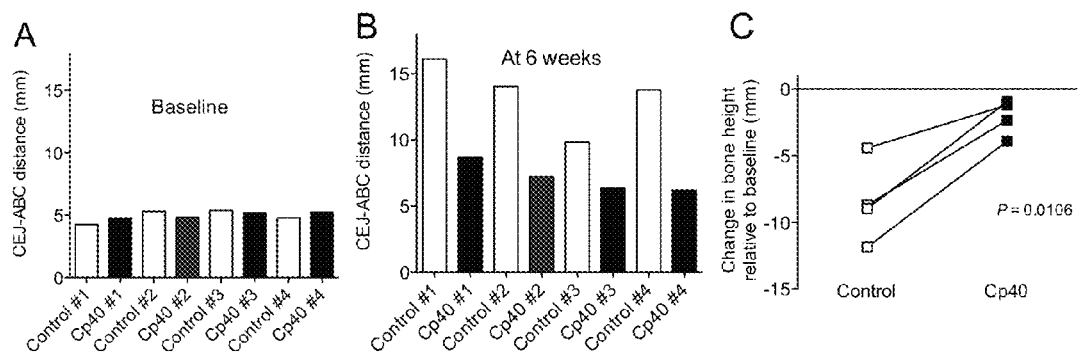
FIG. 8 are graphs showing inhibition of periodontal bone loss following treatment of NHP periodontitis with Cp40. Four monkeys were treated as described in the legend to FIG. 6, and their mandibular bone heights (CEJ-ABC distance) were measured using standardized X-ray images (taken at baseline and at week 6) and NIKON imaging system software. Measurements were made at six points ($1^{st}$ premolar, distal; $2^{nd}$ premolar mesial & distal; $1^{St}$ molar, mesial & distal; $2^{nd}$ molar mesial) and the data in Panel A and Panel B reflect, respectively, the 6-site total at baseline (Panel A) and at week 6 (Panel B). For each control or Cp40 treatment, bone loss was calculated as bone height at baseline minus bone height at 6 weeks (Panel C). The difference between Cp40 and control was significant (P<0.05; paired t test).

In a second NHP study, ligature-induced periodontitis was induced by placing ligatures around the mandibular posterior teeth (i.e., in the lower jaw) of the same two animals plus in two additional animals (total of four monkeys). The results obtained (FIGS. 6, 7, and 8) confirmed the results of the original study. Moreover, the presence of four animals allowed the possibility for statistical analysis. The protective effects of Cp40 with regard to certain clinical parameters (PPD and GI, FIGS. 6A and B) and most cytokine responses (FIG. 7) reached statistical significance. Importantly, Cp40 caused a significant inhibition of bone loss (FIG. 8C), consistent with its effects on molecules regulating osteoclastogenesis (decreased RANKL and increased OPG levels vs. control treatment; FIGS. 7H and I, respectively).

This is the first time, for any disease, that complement inhibition has been shown to inhibit inflammatory processes that lead to osteoclastogenesis and bone loss in NHP. Moreover, these data strongly support the therapeutic potential of Cp40 in human periodontitis.

Other Embodiments

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of treating periodontitis in an individual, comprising:
   (a) identifying an individual suffering from or at risk of developing periodontitis; and
   (b) administering to the individual a composition comprising a pharmaceutically acceptable carrier and a compound that inhibits or blocks C3 expression, activity, or activation, thereby treating the periodontitis; wherein the composition does not comprise an antibody, and wherein the compound is a polypeptide having an amino acid sequence as set forth in SEQ ID NO: 25.

2. The method of claim 1, wherein the composition is administered by a method selected from parenteral, intradermal, subcutaneous, oral, nasal, topical, transdermal and transmucosal.

3. The method of claim 2, wherein the composition is administered to the periodontal pocket of the individual.

4. A method of reducing the amount of *Porphyromonas gingivalis* and/or the inflammation caused by *P. gingivalis* in an individual, comprising:
   (a) identifying an individual in which reduction in the amount of *P. gingivalis* is needed or desired; and
   (b) administering to the individual a composition comprising a pharmaceutically acceptable carrier and a compound that inhibits or blocks C3 expression, activity, or activation, thereby reducing the amount of *P. gingivalis* in the individual;
wherein the composition does not comprise an antibody, and wherein the compound is a polypeptide having an amino acid sequence as set forth in SEQ ID NO: 25.

5. The method of claim 4, wherein the composition is administered by a method selected from parenteral, intradermal, subcutaneous, oral, nasal, topical, transdermal and transmucosal.

6. The method of claim 5, wherein the composition is administered to the periodontal pocket of the individual.

* * * * *